(12) United States Patent
Bunschoten et al.

(10) Patent No.: US 7,732,430 B2
(45) Date of Patent: Jun. 8, 2010

(54) DRUG DELIVERY SYSTEM COMPRISING A TETRAHYDROXILATED ESTROGEN FOR USE IN HORMONAL CONTRACEPTION

(75) Inventors: Evert Johannes Bunschoten, Heesch (NL); Herman Jan Tijmen Coelingh Bennink, Driebergen (NL); Christian Franz Holinka, New York, NY (US)

(73) Assignee: Pantarhei Bioscience B.V., Zeist (NL)

( * ) Notice: Subject to any disclaimer, the term of this patent is extended or adjusted under 35 U.S.C. 154(b) by 1014 days.

(21) Appl. No.: 10/478,365

(22) PCT Filed: May 23, 2002

(86) PCT No.: PCT/NL02/00331

§ 371 (c)(1),
(2), (4) Date: May 25, 2004

(87) PCT Pub. No.: WO02/094279

PCT Pub. Date: Nov. 28, 2002

(65) Prior Publication Data

US 2004/0198710 A1     Oct. 7, 2004

(30) Foreign Application Priority Data

| May 23, 2001 | (EP) | ................................. 01201945 |
| May 23, 2001 | (EP) | ................................. 01201946 |
| May 23, 2001 | (EP) | ................................. 01201947 |
| Nov. 15, 2001 | (EP) | ................................. 01204377 |
| Feb. 21, 2002 | (EP) | ................................. 02075695 |

(51) Int. Cl.
*A61K 31/56* (2006.01)

(52) U.S. Cl. ................. 514/169; 514/170; 514/171; 514/182; 514/841; 514/843

(58) Field of Classification Search ......... 514/169–171, 514/182, 841, 843
See application file for complete search history.

(56) References Cited

U.S. PATENT DOCUMENTS

| 3,440,320 A | 4/1969 | Sackler et al. | |
| 3,797,494 A | 3/1974 | Zaffaroni | |
| 4,460,372 A | 7/1984 | Campbell et al. | |
| 4,573,996 A | 3/1986 | Kwiatek et al. | |
| 4,624,665 A | 11/1986 | Nuwayser | |
| 4,722,941 A | 2/1988 | Eckert et al. | |
| 4,762,717 A | 8/1988 | Crowley, Jr. | |
| 4,937,238 A | 6/1990 | Lemon | |
| 5,063,507 A | 11/1991 | Lindsey et al. | |
| 5,130,137 A | 7/1992 | Crowley, Jr. | |
| 5,211,952 A * | 5/1993 | Spicer et al. | ................. 424/426 |
| 5,223,261 A | 6/1993 | Nelson et al. | |
| 5,340,584 A * | 8/1994 | Spicer et al. | ................. 424/426 |
| 5,340,585 A | 8/1994 | Pike et al. | |
| 5,340,586 A | 8/1994 | Pike et al. | |
| 5,468,736 A | 11/1995 | Hodgen | |
| 5,633,242 A * | 5/1997 | Oettel et al. | ................. 514/170 |
| 5,662,927 A * | 9/1997 | Ehrlich et al. | ................ 424/449 |
| 5,827,843 A | 10/1998 | Koninckx | |
| 6,214,815 B1 * | 4/2001 | Shangold et al. | ............ 514/170 |
| 6,500,814 B1 * | 12/2002 | Hesch | ......................... 514/170 |
| 2002/0183299 A1 | 12/2002 | Voskuhl | |

FOREIGN PATENT DOCUMENTS

| DE | 2336433 A1 | 4/1975 |
| DE | 2336434 A1 | 4/1975 |
| DE | 2426779 A1 | 12/1975 |
| DE | 19917930 A1 | 10/2000 |
| EP | 0402950 A1 | 12/1975 |
| EP | 468690 A1 | 7/1991 |
| EP | 1700602 A1 | 5/2001 |
| WO | 9603929 A1 | 2/1966 |
| WO | 9218107 A1 | 10/1992 |
| WO | 9426207 | 11/1994 |

(Continued)

OTHER PUBLICATIONS

U.S. Appl. No. 10/495,707, filed Nov. 2004, Coelingh Bennink et al.*

(Continued)

*Primary Examiner*—Johann R Richter
*Assistant Examiner*—Mei-Ping Chui
(74) *Attorney, Agent, or Firm*—The Webb Law Firm

(57) ABSTRACT

A method of contraception in mammalian females, which method comprises the oral administration of an estrogenic component and a progestogenic component to a female of childbearing capability in an amount effective to inhibit ovulation, wherein the estrogenic component is selected from the group consisting of substances represented by the following formula (1)

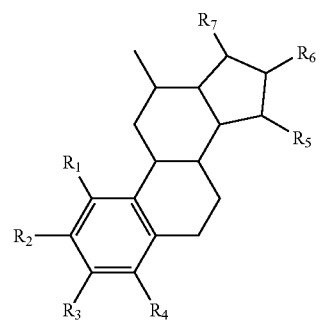

in which $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms; precursors capable of liberating a substance according to the aforementioned formula when used in the present method; and mixtures of one or more of the aforementioned substances and/or precursors. Another aspect of the invention concerns a pharmaceutical kit comprising oral dosage units that contain the aforementioned estrogenic component and/or a progestogenic component.

22 Claims, 3 Drawing Sheets

FOREIGN PATENT DOCUMENTS

| WO | 9502408 A1 | 1/1995 |
|---|---|---|
| WO | WO 95/17895 | 7/1995 |
| WO | 9603929 A1 | 2/1996 |
| WO | 9858657 A1 | 12/1998 |
| WO | 0062753 | 10/2000 |
| WO | WO 00/73416 A1 | 12/2000 |
| WO | 0130357 A | 5/2001 |
| WO | 0185154 A2 | 11/2001 |

OTHER PUBLICATIONS

Levine et al. (Am. J. Obstet. Gynecol. Mar. 15, 1984, p. 735-738).*
Tseng et al. (Journal of Steroid Biochemistry, vol. 9, p. 1145-1128).*
Holinka et al. (Biology of Reproduction, 1980, 22, p. 913-926).*
Tulchinsky et al., Plasma Estetrol as an Index of Fetal Well-Being, J. Clin. Endocrinol. Metab., 40, 560-567, 1975.
Fishman, Fate of 15 α-Hydroxyestriol-'H in Adult Man, Fishman et al., J. Clin. Endocrinol. Metab., 31, 436-438, 1970.
Levine et al., Uterine Vascular Effects of Estetrol in Nonpregnant Ewes, Am J. Obstet. Gynecol., 148:73, 735-738, 1984.
Jozan et al., Different Effects of Oestradiol, Oestriol, Oestrol and of Oestrone on Human Breast Cancer Cells (MCF-7) in Long Term Tissue Culture, Acta Endocrinologica, 98, 73-80, 1981.
Holinka et al., In vivo Effects of Estetrol on the Immature Rat Uterus, Biol. Reprod., 22, 913-926, 1980.
Holinka et al., Comparison of Effects of Estetrol and Tamoxifen with Those of Estriol and Estradiol on the Immature Rat Uterus, Biol. Reprod., 20, 242-246, 1979.
Martucci et al., Direction of Estradiol Metabolism as a Control of its Hormonal Action—Uterotrophic Activity of Estradiol Metabolites, Endocrin., 101, 1709-1715, 1977.
Tseng et al., Competition of Estetrol and Ethynylestradiol with Estradiol for Nuclear Binding in Human Endometrium, J. Steroid Biochem., 7, 817-822, 1976.
Martucci et al., Uterine Estrogen Receptor Binding of Catecholestrogens and of Estetrol (1,3,5(10)-Estratriene-3, 15α, 16α 17β-Tetrol), Steroids, 27, 325-333, 1976.
Allen et al., An Ovarian Hormone, JAMA, 81, 819-821, 1923.
Allen et al., The Induction of a Sexually Mature Condition in Immature Females by Injection of the Ovarian Follicular Hormone, Am. J. Physiol., 69, 577-588, 1924.
Jones et al., The Effects of Various Steroids on the Vaginal Histology in the Rat, Fertil. Steril., 24, 284-291, 1973.
Reel et al., Survey and Assessment of Mammalian Estrogen Biological Assays for Hazard Characterization, Fund. Applic. Toxicol., 34, 288-305, 1996.
Kuipers et al., Enterohepatic Circulation in the Rat, Gastroenterol., 88, 403-411, 1985.
Avvakumov et al., Steroid-binding Specificity of Human Sex Hormone-binding Globulin is Influenced by Occupancy of a Zinc-binding Site, J. Biol. Chem., 275, 25920-25925, 2000.
Schwartz, A Model for the Regulation of Ovulation in the Rat, Recent Prog. Horm. Res., 25, 1-55, 1969.
Beattie et al., The Differential Effects of Diestrous Progestogen Administration on Proestrous Gonadotrophin Levels, Endocrinol., 97, 885-890, 1975.
De Visser et al., Endocrinological Studies with (7α, 17 α)-17-Hydroxy-7-me norpregn-5(10)-en-20-yn-3-one (Org OD 14), Arzneim. Forsh., 34, 1010-1020, 1984.
Office Action mailed on May 22, 2009 in U.S. Appl. No. 10/478,264.
Office Action mailed on Mar. 17, 2008 in U.S. Appl. No. 10/478,357.
Office Action mailed on May 16, 2008 in U.S. Appl. No. 10/478,357.
Office Action mailed on Dec. 16, 2008 in U.S. Appl. No. 10/478,357.
Office Action mailed on May 28, 2009 in U.S. Appl. No. 10/478,357.
Office Action mailed on Jan. 24, 2007 in U.S. Appl. No. 10/495,707.
Office Action mailed on Dec. 28, 2007 in U.S. Appl. No. 10/495,707.
Office Action mailed on Aug. 19, 2008 in U.S. Appl. No. 10/495,707.
Office Action mailed on May 22, 2009 in U.S. Appl. No. 10/495,707.
Office Action mailed on Oct. 15, 2007 in U.S. Appl. No. 10/517,509.
Office Action mailed on Dec. 19, 2007 in U.S. Appl. No. 10/517,509.
Office Action mailed on Mar. 26, 2008 in U.S. Appl. No. 10/517,509.
Office Action mailed on Jan. 5, 2009 in U.S. Appl. No. 10/517,509.
Office Action mailed on Aug. 18, 2009 in U.S. Appl. No. 10/517,509.
Office Action mailed on Apr. 3, 2007 in U.S. Appl. No. 10/517,686.
Office Action mailed on Aug. 9, 2007 in U.S.Appl. No. 10/517,686.
Office Action mailed on Apr. 4, 2008 in U.S. Appl. No. 10/517,686.
Office Action mailed on May 29, 2009 in U.S. Appl. No. 10/517,686.
Office Action mailed on Apr. 23, 2007 in U.S. Appl. No. 10/521,040.
Office Action mailed on Aug. 17, 2007 in U.S. Appl. No. 10/521,040.
Office Action mailed on Apr. 2, 2008 in U.S. Appl. No. 10/521,040.
Office Action mailed on Jun. 1, 2009 in U.S. Appl. No. 10/521,040.
Visser et al., "In vitro effects of estetrol on receptor binding, drug targets and human liver cell metabolism," CLIMACTERIC (2008) 11(1) Appx. II: 1-5.
Visser et al., "First human exposure to exogenous single-dose oral estetrol in early postmenopausal women," CLIMACTERIC (2008) 11(1): 1-10.
Visser et al., "Clinical applications of estetrol," J. Of Steroid Biochem and Molecular Biol. (2009) 114: 85-89.
Holinka et al., "Estetrol: A unique steroid in human pregnancy," J. Of Steroid Biochem and Molecular Biol. (2009) 110: 138-143.
Coelingh Bennink et al., "Oral bioavailability and bone sparing effects of estetrol in an osteoporosis model," CLIMACTERIC (2008) 11 (Supp 3): 1-13.
Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Onlinel; Oct. 31, 2000; pp. 223-229; vol. 36, No. 3; Biosciences Information Service, Philadelphia, PA., U.S.
Hammond et al., A Versatile Method for the Determination of Serum Cortisol Binding Globulin and Sex Hormone Binding Globulin Binding Capacities, 1983, vol. 132, pp. 101-110.
Elger et al., Sulfamates of Various Estrogens are Prodrugs with Increased Systemic and Reduced Hepatic Estrogenicity at Oral Application, J. Steroid Biochem. Molec. Biol., 1995, vol. 55, No. 3 / 4, pp. 395-403.
Murphy et al., Endometrial Effects of Long-Term Low-Dose Administration of RU486, Fertility and Sterility, Apr. 1995, vol. 63, No. 4, pp. 761-766.
Beral et al., Use of HRT and the Subsequent Risk of Cancer, Journal of Epidemiology and Biostatistics, 1999, vol. 4, No. 3, pp. 191-215.
Tavani et al., The Adverse Effects of Hormone Replacement Therapy, Drugs & Aging, May 1999, vol. 14, No. 5, pp. 347-357.
Pike et al., Progestins and Menopause: Epidemiological Studies of Risks of Endometrial and Breast Cancer, Steroids, 2000, vol. 65, pp. 359-664.
Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.
Erdbruegger et al., Drug Discovery Today: Disease Mechanisms (2004), vol. 1, pp. 73-81.
Lab Tests Online (www.labtestsonline.org/understanding/conditions/autoimmune.html) retrieved on Oct. 15, 2009.
www.tiscali.co.uk/lifestyle/healthfitness/health_advice/netdoctor/archive/000489.html, retrieved on Oct. 15, 2009.
MedlinePlus Medical Encyclopedia: Mutiple Sclerosis, retrieved on Mar. 28, 2008 via www.nlm.nih.gov/medlineplus/ency/article/000737.htm, dated on Aug. 6, 2007, p. 1 and 2; also see WebMD: Multiple Sclerosis—Prevention, retrieved on Mar. 28, 2008 via www.webmd.conn/multiple-sclerosis/tc/multiple-sclerosis-ms-prevention, dated on Mar. 23, 2006.
MedlinePlus Medical Encyclopedia: rheumatoid arthritis, retrieved on Mar. 28, 2008 via www.nlm.nih.gov/medlineplus/ency/article/000431.htm, dated on Jul. 27, 2007, p. 1-2 and 4; also WebMD: Rheumatoid Arthritis—Prevention, retrieved on Mar. 28, 2008 via www.webmd.com/rheumatoid-arthritis/tc/rheumatoid-arthritis-prevention, dated on Aug. 23, 2006.
Mueck et al., "Angio and Anti-Angiogenetic Effects of Estradiol and its Metabolites", J. Clin. Basic Cardiol., 2001, pp. 153-155, vol. 4, No. 2.
Shah et al., "Estrogen and Skin. An Overview", Am. J. Clin. Dermatol., 2001, pp. 143-150, vol. 2, No. 3.

Sitruk-Ware et al., "Local Hormonal Treatment for Urogenital Atrophy After Menopause", Shweiz. Rundsch, Med. Praxis, 1997, pp. 1245-1248, vol. 86, No. 33, and Sitruk-Ware, English Translation, 1997. Praxis, Schweirzerische Rundschau fur Medizin, vol. 86, No. 33, pp. 1-13.

Schmidt et al., "Treatment of Skin Aging with Topical Estrogens", Int. J. Dermatol., 1996, pp. 669-674, vol. 35, No. 9.

Younglai et al., Journal of Clinical Endocrinology and Metabolism, 1968, vol. 28, Issue 11, pp. 1611-1617.

Webster Ninth New Collegiate Dictionary, 2000, Definition of Prevention, p. 1.

Willhite et al., Pharmacotherapy, 2001, vol. 21, Issue 4, pp. 464-480.

Tseng et al., "Heterogeneity of Saturable Estradiol Binding Sites in Nuclei of Human Endometrium. Estetrol Studies", (1978), vol. 9, pp. 1145-1148.

Seeger et al., "The inhibitory effect of endogenous estrogen metabolies on copper-mediated in vitro oxidation of LDL", Int. Journal of Clinical Pharmacology and Therapeutics, (1998), vol. 36, No. 7, pp. 383-385.

National Cancer Institute: Breast cancer prevention retrieved online Aug. 07, 2007 from the internet; http://www.cancer.gov/templates/doc.aspx?viewed+D972A74B-D25A-4F86-B8ED-33EB3C0450E4& version, p. 1.

Medline Plus: Medical Encyclopedia: Ovarian cancer retrieved online on Aug. 09, 2007 from the internet: https://www.nlm.nih.gov/medlineplus/ovariancancer.html, p. 1 dated Jul. 31, 2007.

National Institute of Child Health and Human Development, NIH Publication No. 02-2413 retrieved online on Aug. 09, 2007.

Breast Cancer Prevention retrieved online Aug. 7, 2007 from the Internet; http://www.cancer.gov/cancertopics/pdq/prevention/breast/Patient/page 3.

Prophylactic definition—Medical Dictionary of Popular Medical Terms; retrieved on Mar. 14, 2008 via www.medterms.com/script/main/art.asp?articlekey+11902.

Zips et al., in vivo, 2005, vol. 19, pp. 1-8.

Martucci et al., "Impact of Continuously Administered Catechol Estrogens on Uterine Growth and Luteinizing Hormone Secretion", Endocrinology (Dec. 1979), vol. 105, No. 6, pp. 1288-1292.

Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol: A Prospective Randomized Study", Fertility and Sterility, (Jul. 2002), vol. 78, No. 1, pp. 34-39.

Trotter et al., "Effects of Postnatal Estradiol and Progesterone Replacement in Extremely Preterm Infants", J. Clin. Endocrinol Metab., (Dec 1999), vol. 84, No. 12, pp. 4531-4535.

Shanklin et al., "Aqueous Estrogens in the Management of Respiratory Distress SYndrome", J. Reprod. Med. (Aug. 1970), vol. 5, No. 2, pp. 53-71.

Chemical Abstracts Service, Columbus Ohio, US: Jakowicki, "Evaluation of Estriol Level in the Amniotic Fluid in Prolonged Pregnancy", XP002458625.

Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-604.

Fogary, Jr., "Postmaturity", J. Am. Osteopath. Assoc., (Jan. 1976), vol. 75, No. 5, pp. 512-517.

Coelingh-Bennink et al., "Estetrol review: profile and potential clinical applications", International Menopause Society, CLIMATERIC, vol. 11, (Suppl 1), pp. 47-58 (2008).

Speroff et al., Clinical Gynecologic Endocrinology and Infertility, Seventh Edition, p. 270 (partial).

White et al., "The pharmacokinetics of Intravenous Estradiol: A Preliminary Study", Pharmacotherapy, vol. 18, pp. 1343-1346, (1998) (Abstract).

Hammond et al., "Estetrol does not bind sex hormone binding globulin or increase its production by human HepG2 cells", International Menopause Society, CLIMATERIC, vol. 11, (Suppl. 1), pp. 41-46, (2008).

Office Action mailed on Jan. 11, 2008 in U.S. Appl. No. 10/478,262.
Office Action maOffice Action mailed on Feb. 19, 2009 in U.S. Appl. No. 10/478,262.iled on May 15, 2008 in U.S. Appl. No. 10/478,262.
Office Action mailed on Jun. 9, 2009 in U.S. Appl. No. 10/478,262.
Office Action mailed on Nov. 18, 2008 in U.S. Appl. No. 10/478,264.

* cited by examiner

FORMULA I

| Treatment Group | Dosing route | Number of Rats Exhibiting Estrogenic Response/ Number of Rats Treated | | | | | | | |
|---|---|---|---|---|---|---|---|---|---|
| | | Day of Study | | | | | | | |
| | | Day 0 | Day 1 | Day 2 | Day 3 | Day 4 | Day 5 | Day 6 | Day 7 |
| 0.05 mg/kg/day EE | po | 0/8 | 1/8 | 3/8 | 8/8 | 8/8 | 8/8 | 8/8 | 8/8 |
| Vehicle Control (2 ml/kg/day) | po | 0/8 | 0/8 | 0/8 | 0/8 | 0/8 | 0/8 | 0/8 | 0/8 |
| 0.1 mg/kg/day E4 | po | 0/8 | 0/8 | 1/8 | 7/8 | 8/8 | 8/8 | 8/8 | 8/8 |
| 0.3 mg/kg/day E4 | po | 0/8 | 0/8 | 1/8 | 7/8 | 8/8 | 8/8 | 8/8 | 8/8 |
| 1.0 mg/kg/day E4 | po | 0/8 | 0/8 | 4/8 | 8/8 | 8/8 | 8/8 | 8/8 | 8/8 |
| 3.0 mg/kg/day E4 | po | 0/8 | 0/8 | 6/8 | 8/8 | 8/8 | 8/8 | 8/8 | 8/8 |

FIGURE 2

DRUG DELIVERY SYSTEM COMPRISING A TETRAHYDROXILATED ESTROGEN FOR USE IN HORMONAL CONTRACEPTION

TECHNICAL FIELD OF THE INVENTION

The present invention relates to a method of hormonal contraception in mammalian females. More particularly the invention is concerned with a method of hormonal contraception that comprises the oral administration of a combination of an estrogenic component and a progestogenic component to a female of childbearing capability in an effective amount to inhibit ovulation.

The invention also encompasses a pharmaceutical kit comprising a plurality of oral dosage units that contain an estrogenic component and a progestogenic component.

BACKGROUND OF THE INVENTION

Estrogens play an important major role in existing methods of hormonal contraception. For contraception estrogens are commonly used together with a progestogen, e.g. levonorgestrel, desogestrel, norethisterone, cyproterone acetate, dienogest. The estrogens are needed for inhibiting follicle maturation and ovulation, but in addition they replace the endogenous ovarian secretion of estradiol which is suppressed to a major extent by the administration of a hormonal contraceptive. This replacement is important for preventing estrogen deficiency and for maintaining an artificial menstrual cycle and other genital functions.

Endogenous and exogenous estrogens fulfil important central nervous and metabolic functions in the female organism: normal estrogen levels make a decisive contribution to a woman's well-being. Notwithstanding the widespread use of estrogens in hormonal contraceptives, there are still some unsolved problems. Known estrogens, in particular the biogenic estrogens (i.e. estrogens naturally occurring in the human body), show serious pharmacokinetic deficits. Biogenic estrogens such as estradiol, estrone, estrone sulphate, esters of estradiol and estriol become bioavailable only to a very low degree when taken orally. This degree may vary so much from person to person that general dosage recommendations cannot be given. Fast elimination of these estrogens from the blood is another related problem. For instance, for the main human biogenic estrogen 17β-estradiol the half-life is around 1 hour. As a result, between separate (daily) administration events, blood serum levels of such biogenic estrogens tend to fluctuate considerably. Thus, shortly after administration the serum concentration is usually several times higher than the optimum concentration. In addition, if the next administration event is delayed, serum concentrations will quickly decrease to a level where the estrogen is no longer physiologically active.

The most important synthetically altered estrogenic steroid is 17α-ethinyl estradiol (EE). This estrogen is dominant in oral hormonal contraception. Apart from EE, mestranol has been used in a few cases; mestranol is a "prodrug" that is metabolised to EE in the organism. When applied orally to humans, EE has a much better bioavailability than the biogenic estrogens mentioned above, but its oral bioavailability varies to a large extent from individual to individual. Several authors have pointed to this as well as to the fact that concentrations in the blood proved to be highly fluctuating after oral application of this substance.

In addition to pharmacokinetic problems, the known estrogens also show pharmacodynamic deficits. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. The secretion activity that is controlled by estrogens in the human liver includes increased synthesis of transport proteins CBG, SHBG, TBG, several factors that are important for the physiology of blood clotting, and lipoproteins. If biogenic estrogens are introduced to the female organism while avoiding passage through the liver (e.g. by transdermal application), the liver functions mentioned remain largely unchanged. Therapeutically equivalent doses of biogenic estrogens, when applied orally, result in clear responses of hepatic parameters, such as increase of SHBG, CBG, angiotensinogen and HDL (high density lipoprotein). These hepatic effects of estrogens are also observed when equine estrogen formulations (so-called conjugated estrogens) are used. Ethinyl estradiol and diethylstilbestrol (DES) have an even greater hepatic estrogenicity. Elger et al., J. Steroid Biochem. Molec. Biol. (1995), 55(3/4), 395-403, have reported that EE or DES have much higher hepatocellular than systemic estrogenicity: in relation to FSH-secretion inhibitory activity these estrogens are 4-18 times more active in the liver than estrone sulfate.

The aforementioned deficits are of considerable clinical significance when commonly known biogenic and synthetic estrogens are applied. Consequently, there is an as yet unmet need for estrogens that do not display these deficits and which can suitably be employed in oral contraceptive methods for females because of their ability to (a) reliably suppress follicle maturation and ovulation and to (b) effectively replace the endogenous ovarian secretion of estradiol.

SUMMARY OF THE INVENTION

The inventors have surprisingly found that these objectives are met by estrogenic substances that are represented by Formula I (FIG. 1) in which $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms.

A known representative of this group of estrogenic substances is 1,3,5(10)-estratrien-3,15α,16α,17β-tetrol, also known by the names of estetrol, oestetrol and 15α-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et al., 1975. J. Endocrinol. Metab., 40, 560-567).

In 1970, Fishman et al., "Fate of 15α-hydroxyestriol-$^3$H in Adult Man", J Clin Endocrinol Metab (1970) 31, 436-438, reported the results of a study wherein tritium labeled 15α-hydroxyestriol (estetrol) was administered intravenously to two adult women. It was found that the estetrol was rapidly and completely excreted in urine as the glucosiduronate and that virtually no metabolism except for conjugation took place.

Between 1975 and 1985 several researchers have investigated the properties of estetrol and reported on its estrogenic potency and uterotrophic activity. The most relevant publications that were issued during this period are mentioned below:

Levine et al., 1984. Uterine vascular effects of estetrol in nonpregnant ewes. Am. J. Obstet. Gynecol., 148:73, 735-738: "When intravenously administered in non-pregnant ewes, estetrol is 15 to 30 times less potent than estriol and 17β-estradiol in uterine vasodilation".

Jozan et al., 1981. Different effects of oestradiol, oestriol, oestetrol and of oestrone on human breast cancer cells (MCF-7) in long term tissue culture. Acta Endocrinologica, 98, 73-80: "Estetrol agonistic potency is 2% of the magnitude observed for 17β-estradiol in in vitro cell proliferation".

Holinka et al., 1980. Comparison of effects of estetrol and tamoxifen with those of estriol and estradiol on the immature rat uterus. Biol. Reprod. 22, 913-926: "Subcutaneously administered estetrol has very weak uterotrophic activity and is considerable less potent than 17β-estradiol and estriol".

Holinka et al., 1979. In vivo effects of estetrol on the immature rat uterus. Biol. Reprod. 20, 242-246: "Subcutaneously administered estetrol has very weak uterotrophic activity and is considerable less potent than 17β-estradiol and estriol".

Tseng et al., 1978. Heterogeneity of saturable estradiol binding sites in nuclei of human endometrium. Estetrol studies. J. Steroid Biochem. 9, 1145-1148: "Relative binding of estetrol to estrogen receptors in the human endometrium is 1.5% of 17β-estradiol".

Martucci et al., 1977. Direction of estradiol metabolism as a control of its hormonal action-uterotrophic activity of estradiol metabolites. Endocrin. 101, 1709-1715: "Continuous administration of estetrol from a subcutaneous depot shows very weak uterotrophic activity and is considerably less potent than 17β-estradiol and estriol".

Tseng et al., 1976. Competition of estetrol and ethynylestradiol with estradiol for nuclear binding in human endometrium. J. Steroid Biochem. 7, 817-822: "The relative binding constant of estetrol binding to the estrogen receptor in the human endometrium is 6.25% compared to 17β-estradiol (100%)".

Martucci et al., 1976. Uterine estrogen receptor binding of catecholestrogens and of estetrol (1,3,5(10)-estratriene-3,15alpha,16alpha,17beta-tetrol). Steroids, 27, 325-333: "Relative binding affinity of estetrol to rat uterine cytosol estrogen receptor is 0.5% of 17β-estradiol (100%). Furthermore, the relative binding affinity of estetrol to rat uterine nuclear estrogen receptor is 0.3% of 17β-estradiol (100%)".

All of the above publications have in common that the authors have investigated the estrogenic potency of estetrol. Without exception they all conclude that estetrol is a weak estrogen. In some of the cited articles the estrogenic potency of estetrol has been found to be lower than that of another biogenic estrogen, namely, 17β-estradiol, which is considered to be a relatively weak estrogen (e.g. compared to ethinyl estradiol). With these findings in mind, it is not surprising that the interest in estetrol has dwindled since the early eighties and that no publications on the properties of estetrol have been issued since.

U.S. Pat. No. 5,468,736 (Hodgen) describes a method of hormone replacement therapy involving the administration of estrogen together with an amount of antiprogestin (antiprogestogen), which inhibits estrogen-induced endometrial proliferation in women. In Example 3 the combined use of estetrol and lilopristone is mentioned. No clues are given in the examples as to the mode and frequency of administration or regarding the dosage level employed. A disadvantage associated with the use of antiprogestogens, such as lilopristone, is the risk of inducing abnormal endometrial morphology, i.e. cystic hyperplasia, as has been observed in women who received an antiprogestogen treatment against endometriosis (Murphy et al., 1995. Fertil. Steril., 95, 761-766).

U.S. Pat. No. 5,340,586 (Pike et al.) is concerned with compositions and methods which are effective to treat oophorectomised women, wherein an effective amount of an estrogenic composition and an androgenic composition are provided over a period of time. In the US-patent it is stated that natural and synthetic estrogenic compositions that can be used include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol and estrone potassium sulfate, and furthermore that equine estrogens, such as equilelinin, equilelinin sulfate and estetrol, may also be employed. Except for the exhaustive inventory of known estrogens, no other reference to estetrol (which is erroneously referred to as an equine estrogen) is made in this US-patent.

The same exhaustive list of estrogens is found in the following patent documents:

U.S. Pat. No. 4,762,717 (Crowley): A contraceptive method comprising the sequential administration of (1) a combination of luteinizing hormone releasing hormone (LHRH) and estrogen and (2) a combination of LHRH and estrogen and progestogen.

U.S. Pat. No. 5,130,137 (Crowley): A method of treating benign ovarian secretory disorder comprising the sequential administration of (1) a combination of luteinizing hormone releasing hormone (LHRH) and estrogen and (2) a combination of LHRH and estrogen and progestogen.

U.S. Pat. No. 5,211,952 (Spicer et al.): A contraceptive method comprising administering a gonadotropin hormone releasing hormone (GnRH) composition in an amount effective to inhibit ovulation and administering estrogen and progestogen to maintain serum levels above a defined minimum level.

U.S. Pat. No. 5,340,584 (Spicer et al.): A method for preventing conception or for treating benign gynaecological disorders comprising administering a GnRH composition for a first period of time in an amount effective to suppress ovarian estrogen and progesterone production, simultaneously administering an estrogenic composition in an amount effective to prevent symptoms of estrogen deficiency and simultaneously administering a progestogen in an amount effective to maintain serum level of said progestogen at a level effective to decrease endometrial cell proliferation.

U.S. Pat. No. 5,340,585 (Pike et al.): A method of treating benign gynaecological disorders in a patient in whom the risk of endometrial stimulation by estrogenic compositions is minimised or absent, comprising administering a GnRH composition in an amount effective to suppress ovarian estrogen and progesterone production and administering an estrogenic composition in an amount effective to prevent symptoms of estrogen deficiency.

WO 00/73416 (Yifang et al.): A method for regulating the fertility of a host, comprising contacting host ovarian cells with a safe and effective amount of a pharmaceutical composition comprising an antisense oligonucleotide that is complementary to the nucleotide sequence of the follicle stimulating hormone (FSH) receptor. The possibility of combined administration of such an antisense oligonucleotide with an estrogenic steroid is mentioned in the application.

The benefits of the present invention may be realised without the co-administration of anti-progestogens, LHRH compositions, GnRH compositions and/or antisense oligonucleotides that are complementary to the nucleotide sequence of the follicle stimulating hormone (FSH) receptor as proposed in the aforementioned publications. Also, the present invention may suitably be applied in individuals who have not been oophorectomised, or in whom the risk of endometrial stimulation by estrogenic compositions is not minimised or absent, other than by combined administration of a progestogen and an estrogen, e.g. as a result of hysterectomy. Furthermore the present method does not require the use of a slow release formulation as is dictated by most of the aforementioned US-patents.

It is noted that none of the aforementioned publications describe the oral administration of estetrol. The only modes of administration described therein are intravenous and subcutaneous (depot) administration. For each of these modes of administration it can be concluded that the performance of estetrol is very much inferior to that of e.g. 17β-estradiol. Given that there was no reason to assume that a different outcome might be obtained in case of oral administration, it is not surprising that oral administration of estetrol has not been pursued and that no reports to this effect can be found in the prior art.

In view of the low estrogenic potency of the estetrol-like substances that are employed in accordance with the invention, it is surprising that these substances can effectively be used in a contraceptive method, particularly in a contraceptive method that employs oral administration of such substances. Although the inventors do not wish to be bound by theory, it is believed that the unexpected efficacy of orally administered estetrol-like substances results from the combination of unforeseen favourable pharmacokinetic (ADME) and pharmacodynamic properties of these substances As regards the pharmacokinetic properties of the present estrogenic substances the inventors have discovered that their oral bioavailability is surprsingly high and that their in vivo half-life is considerably longer than that of other biogenic estrogens. Thus, even though estetrol and estetrol-like substances have relatively low estrogenic potency, they may effectively be employed in an oral contraceptive method because their low potency is compensated for by a relatively high oral bioavailability in combination with a high metabolic stability, as demonstrated by a long half-life.

An important advantage of oral administration of estetrol and estetrol-like substances resides in the fact that the hepatic effects of estetrol-like substances are deemed to be minimal since they are hardly metabolised during the so called "first pass". The first-pass effect of drugs given orally, refers to the process of drug degradation by the liver during a drug's transition from initial ingestion to circulation in the blood stream.

Another advantageous property of the present estrogenic substances resides in the fact that sex hormone-binding globulin (SHBG) hardly binds these estrogenic substances, meaning that, in contrast to most known estrogens, serum levels are representative for bio-activity and independent of SHBG levels.

Yet another important benefit of the present estrogenic substances is derived from their relative insensitivity to interactions with other drugs (drug-drug interactions). It is well known that certain drugs may decrease the effectiveness of estrogens, such as ethinyl estradiol, and other drugs may enhance their activity, resulting in possible increased side-effects. Similarly estrogens may interfere with the metabolism of other drugs. In general, the effect of other drugs on estrogens is due to interference with the absorption, metabolism or excretion of these estrogens, whereas the effect of estrogens on other drugs is due to competition for metabolic pathways.

The clinically most significant group of estrogen-drug interactions occurs with drugs that may induce hepatic microsomal enzymes which may decrease estrogen plasma levels below therapeutic level (for example, anticonvulsant agents; phenyloin, primidone, barbiturates, carbamazepine, ethosuximide, and methosuximide; antituberculous drugs such as rifampin; antifungal drugs such as griseofulvin). The present estrogenic substances are less dependent on up- and downregulation of microsomal liver enzymes (e.g. P450's) and also are less sensitive to competition with other P450 substrates. Similarly, they do not interfere significantly in the metabolism of other drugs.

The conjugates of most estrogens, as formed in the liver, are excreted in the bile and may be broken down by gut bacteria in the colon to liberate the active hormone which can then be reabsorbed (enterohepatic recirculation). There are clinical reports that support the view that enterohepatic recirculation of estrogens decreases in women taking antibiotics such as ampicillin, tetracycline, etc. Conjugated forms of the present estrogenic substances are hardly excreted in the bile, meaning that they are substantially insensitive to drugs that do influence the enterohepatic recirculation of other estrogens. Consequently, the risk of pregnancy in contraceptive protocols that employ the present estrogenic substances, is significantly lower than in similar protocols that employ commonly known estrogens.

The above observations serve to explain why the estrogenic substances of the invention hardly suffer from drug-drug interactions and thus produce a very consistent, i.e. predictable, impact. Thus, the efficacy of the estrogenic substances of the invention is highly reliable, which is particularly important in the field of contraception.

BRIEF DESCRIPTION OF THE DRAWINGS

FIG. 2 is a table showing vaginal estrogenic response in ovariectomized rats treated orally (po) with 17α-ethinyl estradiol (EE) or estetrol (E4). The data is expressed as the number of rats showing vaginal cornification over the number of rats (ratio) treated.

DETAILED DESCRIPTION OF THE INVENTION

Figure 1:
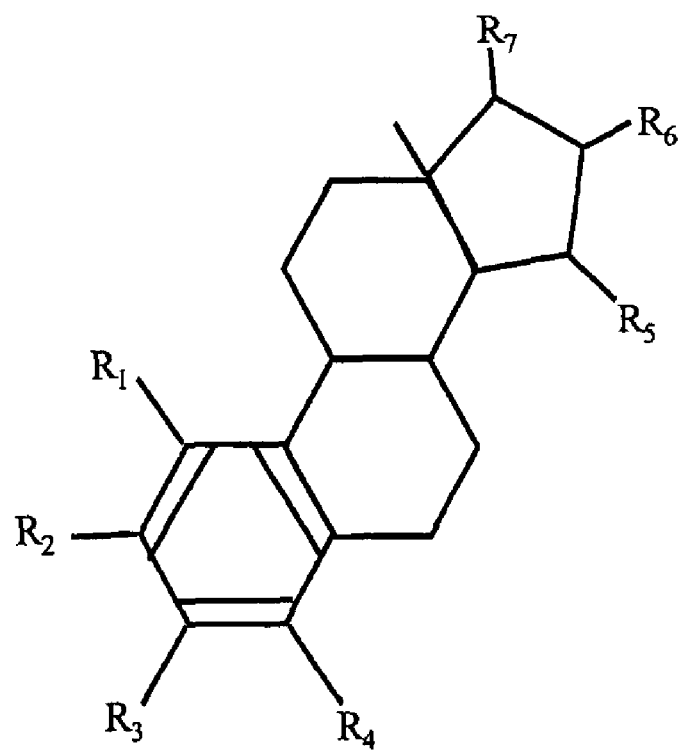
FIG. 1 is a chemical drawing of Formula I.

Accordingly one aspect of the present invention relates to a method of contraception in mammalian females, which method comprises the oral administration of an estrogenic component and a progestogenic component to a female of childbearing capability in an amount effective to inhibit ovulation, wherein the estrogenic component is selected from the group consisting of:

substances represented by Formula I in which $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;

precursors capable of liberating a substance according to the aforementioned formula when used in the present method;

and mixtures of one or more of the aforementioned substances and/or precursors. The term "oral administration" as used in here also encompasses oral gavage administration.

The term "estrogenic component" as used throughout this document encompasses substances that are capable of triggering an estrogenic response in vivo, as well as precursors that are capable of liberating such an estrogenic component in vivo when used in accordance with the present invention. In order for estrogenic components to trigger such a response they normally have to bind to an estrogen receptor, which receptors are found in various tissues within the mammalian body. The term "progestogenic component" is defined as a substance that is capable of triggering an progestogenic response in vivo or a precursor which is capable of liberating such a substance in vivo. Usually progestogenic components are capable of binding to a progestogen receptor.

It is noted that the present invention not only encompasses the use of estrogenic and progestogenic components specifically mentioned in this application, but also metabolites of these hormones that display comparable in vivo functionality. In this context it is observed that, for instance, levonorgestrel is a metabolite of norgestimate and that estriol is a metabolite of 17beta-estradiol. Both these progestogens and estrogens have found application in contraceptive formulations and/or hormone replacement therapy. The term "estrogenic substances" as used in this document does not encompass tritium ($^3$H) labeled estrogenic substances such as tritium labeled estetrol.

The present estrogenic substances are distinct from both the biogenic and synthetic estrogens that are commonly applied in pharmaceutical formulations in that they contain at least 4 hydroxyl groups. The present substances are special in that the 5 membered ring in the steroid skeleton comprises 3 hydroxyl substituents rather than 0-2.

Known estrogens that contain at least 4-hydroxyl groups and derivatives thereof are:

1,3,5(10)-estratrien-2,3,15α,16α,17β-pentol 2-methyl ether 1,3,5(10)-estratrien-2,3,15β,16α,17β-pentol 2-methyl ether 1,3,5(10)-estratrien-2,3,16α,17β-tetrol 1,3,5(10)-estratrien-3,4,16α,17β-tetrol 4-methyl ether 1,3,5(10)-estratrien-3,15α,16α,17β-tetrol 1,3,5(10)-estratrien-3,15α,16α,17β-tetrol tetra acetate 1,3,5(10)-estratrien-3,15β,16β,17β-tetrol tetra acetate Preferably, the estrogenic substance applied as the active component in the present composition is a natural estrogen, i.e. an estrogen that is found in nature and especially in mammals. Even more preferably, the estrogenic substance is a so called biogenic estrogen, i.e. an estrogen that occurs naturally in the human body, a precursor of a biogenic estrogen or mixtures thereof. Because biogenic estrogens are naturally present in the fetal and female body, side-effects are not expected to occur, particularly not if the serum levels resulting from the exogenous administration of such estrogens do not substantially exceed naturally occurring concentrations. Since estetrol serum levels in the fetus are several times higher than those found in pregnant females and knowing that the fetus is particularly vulnerable, estetrol is deemed to be a particularly safe biogenic estrogen. Side-effects are not expected to occur, particularly not if the serum levels resulting from the exogenous administration of such estrogens do not substantially exceed naturally occurring (fetal) concentrations. With synthetic estrogens such as ethinyl estradiol there is a (dose dependent) risk of undesirable side-effects, such as thromboembolism, fluid retention, nausea, bloating, cholelithiasis, headache and breast pain.

In a preferred embodiment of the present invention the estrogenic substance contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents $R_5$, $R_6$ and $R_7$ are chirally active. In one preferred embodiment, the present estrogenic substance is 15α-hydroxy substituted. In another preferred embodiment the substance is 16α-hydroxy substituted. In yet another preferred embodiment, the substances is 17β-hydroxy substituted. Most preferably the estrogenic substances are 15α,16α,17β-trihydroxy substituted.

In another preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5(10)-estratrien-3,15, 16,17-tetrol. A preferred isomer of the latter substance is 1,3,5(10)-estratrien-3,15α,16α,17β-tetrol (estetrol).

The invention also encompasses the use of precursors of the estrogenic substances that constitute the active component in the present method. These precursors are capable of liberating the aforementioned estrogenic substances when used in the present method, e.g. as a result of metabolic conversion. These precursors are preferably selected from the group of androgenic precursors as well as derivatives of the present estrogenic substances. Suitable examples of androgenic precursors include androgens that can be converted into the present estrogenic substances through in vivo aromatisation. Examples of derivatives of the present estrogenic substances that can suitably be used as precursors include such substances wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranal; or a straight or branched chain glycosidic residue containing 1-20 glycosidic units per residue.

Typical examples of precursors which can suitably be used in accordance with the invention are esters that can be obtained by reacting the hydroxyl groups of the estrogenic substances with substances that contain one or more carboxy ($M^{+-}OOC$—) groups, wherein $M^+$ represents a hydrogen or (akali)metal cation. Hence, in a particularly preferred embodiment, the precursors are derivatives of the estrogenic substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The present method usually employs uninterrupted oral administration of the estrogenic component during a period of at least 10 days, preferably of at least 20 days. The term "uninterrupted" as used in here, means that the estrogenic component is administered at relatively regular intervals, with no (therapeutically) significant interruptions. Naturally, minor interruptions may occur that do not affect the overall effectiveness of the present method, and indeed such aberrations are encompassed by the present invention. In a preferred embodiment, and more arithmetically, the administration regimen is deemed to be continuous if the longest interval between 2 subsequent administrations is not more than 3.5 times as long as the average interval. Even more preferably said longest interval is not more than 2.5 times, most preferably not more than 1.5 times as long as the average interval.

In the present method, the estrogenic and progestogenic component may be administered in separate oral dosage units. However, it is also possible and indeed very convenient to combine these two components into a single oral dosage unit.

In the contraceptive method according to the present invention the combination of the progestogenic and estrogenic component is suitably administered uninterruptedly during a period of at least 10 days so as to achieve effective ovulation inhibition for a period of at least 20 days.

The invention may suitably be reduced to practice in the form of a variety of contraceptive methods that are known to the person skilled in the art. Amongst these methods are the so called "combined" methods. The combined methods make use of monophasic preparations, which contain dosage units with a constant amount of an estrogen and a progestogen or bi- or triphasic preparations which have varying levels of estrogen and progestogen; in most cases consisting of relatively constant levels of estrogen with a step-wise increase in progestogen throughout the cycle. The combined methods have in common that they are based on a regimen which involves an administration-free interval of about 7 days whereby withdrawal bleeding, simulating the natural menses, occurs. Thus 21 day intervals of hormone administration alternate with 7 days during which no hormones are administered.

As an alternative to the aforementioned combined methods, the so called "sequential" method has been proposed. Typical of the sequential method is that it comprises two consecutive phases, i.e. one phase during which estrogen and no progestogen is administered and another phase during which a combination of estrogen and progestogen is administered. The first contraceptive sequential methods, like the aforementioned combined methods, made use of an administration free interval of about 7 days. More recently, sequential methods have been proposed which do not include an administration-free (or placebo) period, meaning that estrogen is administered throughout the full cycle and that progestogen is co-administered during only part of that cycle. WO 95/17895 (Ehrlich et al.) describes such an uninterrupted sequential method.

Yet another example of a contraceptive method which is encompassed by the present invention is the so called "continuous combined" method, which is a particular version of the combined method that uses uninterrupted combined administration of a progestogenic and an estrogenic component during a prolonged period of time, e.g. more than 50 days. In contrast to ordinary combined and sequential methods, no regular menses occur in the continuous combined method as the continuous administration of progestogen in the indicated amounts induces amenorrhoea.

In one embodiment of the invention, which relates to the continuous combined method, the present method comprises the uninterrupted oral administration of the combination of the estrogenic component and the progestogenic component during a period of at least 28, preferably at least 60 days.

In another embodiment of the invention, which relates to sequential and combined methods that employ a significant administration-free interval, the method of the invention comprises an interval of at least 2 days, preferably from 3-9 days, most preferably from 5-8 days, during which no progestogenic component and no estrogenic component is administered and wherein the resulting decrease in serum concentration of the progestogenic component and the estrogenic component induces menses.

Yet another embodiment of the invention, which concerns a sequential method without a significant pause, is characterised in that it comprises the uninterrupted oral administration of the estrogenic component during a period of at least 28 days, preferably at least 60 days, and in that, following the combined administration of the estrogenic component and the progestogenic component, the estrogenic component and no progestogenic component are administered during 3-18 consecutive days, preferably during 5-16 consecutive days and the resulting decrease in serum concentration of the progestogenic component should normally be sufficient to induce menses.

In the present methods uninterrupted administration of the estrogenic component may usually occur at intervals of between 6 hours and 7 days, preferably of between 12 hours and 3 days. The relatively high in vivo half-life of the present estrogenic components in comparison to most known estrogens makes it feasible to employ oral administration intervals that are significantly longer than 1 day. For practical reasons, and particularly with a view to user compliance, it is preferred to orally administer the estrogenic component as well as the progestogenic component at least once daily, most preferably once daily.

In all of the aforementioned methods it is preferred to orally administer the estrogenic component and the progestogenic component at least once daily during a period of at least 10, preferably of at least 20 days. In case of a sequential method without pause or a continuous combined method it is preferred to orally administer the estrogenic component and/or the progestogenic component at least once daily during a period of at least 30 days, more preferably of at least 60 days, most preferably of at least 150 days. Uninterrupted sequential contraceptive methods, which employ continuous estrogen administration, exhibit an optimum combination of contraceptive reliability and cycle control. The combination of a pause of 6-7 days during which significant follicular development occurs and the well documented bad compliance of many pill-users (30%-40% forget pills occasionally) cause an increased risk of escape ovulation especially if the pause is (unintentionally) extended. This results in "real life" pregnancy rates of 3-8% per year. By removing the pause and administering ovulation inhibiting steroids daily, the risk of escape ovulation is much lower.

The general concerns about the so called unopposed administration of estrogen, i.e. administration of estrogen without co-administered progestogen might cause hyperplasia of the endometrium, are less applicable to the estrogenic components of the present invention. Therefore, in a particularly preferred embodiment, the present contraceptive method is executed in accordance with a sequential contraceptive method without pause.

Good results can be obtained with the present method if the estrogenic component is orally administered in an amount of less than 1 mg per kg of bodyweight per day, preferably of less than 400 µg per kg of bodyweight per day, more preferably of less than 200 µg per kg of bodyweight per day. In order to achieve a significant impact from the administration of the present estrogenic component, it is advisable to orally administer in an amount of at least 1 µg per kg of bodyweight per day. Preferably, the orally administered amount is at least 2 µg per kg of bodyweight per day. More preferably, the orally administered amount is at least 5 µg per kg of bodyweight per day.

In the present method, particularly when used in humans, the estrogenic component is usually administered in an average dosage of at least 0.05 mg per day, preferably of at least 0.1 mg per day. The maximum dosage is normally kept below 40 mg per day, preferably below 20 mg per day. The normally employed dose of the progestogenic component is equivalent to an average oral dosage of 30-750 μg levonorgestrel per day, preferably to 50-400 μg levonorgestrel per day.

In the present method, the estrogenic component is preferably administered in an amount effective to achieve a blood serum concentration of at least 1 nanogram per liter, more preferably of at least 10 nanogram per liter, most preferably at least 100 nanogram per liter. Generally the resulting blood serum concentration of the estrogenic component will not exceed 100 μg per liter, preferably it will not exceed 50 μg per liter, more preferably it will not exceed 25 μg per liter.

In accordance with the present invention the progestogenic component is advantageously administered in an amount which is equivalent to a daily oral dosage of 0.3 to 20 μg levonorgestrel per kg of bodyweight, preferably of 0.5-5 μg levonorgestrel per kg of bodyweight.

Examples of progestogens which may suitably be used in accordance with the present invention include: progesterone, levonorgestrel, norgestimate, norethisterone, dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, fluorogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nomegestrol, norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-nor-pregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and precursors of these compounds that are capable of liberating these progestogens in vivo when used in the present method. Preferably the progestogen used in the present method is selected from the group consisting of progesterone, desogestrel, etonogestrel, gestodene, dienogest, levonorgestrel, norgestimate, norethisterone, drospirenone, trimegestone, dydrogesterone, precursors of these progestogens and mixtures thereof.

The present method also encompasses the co-administration of active principles in addition to the progestogenic and estrogenic component. For instance, androgens may advantageously be co-administered in order to prevent symptoms of hypoandrogenicity. Thus, a preferred embodiment of the invention comprises the co-administration of an androgenic component. The androgenic component is suitably co-administered in an effective amount to suppress symptoms of hypoandrogenicity. Hypoandrogenicity in females has been associated with mood disturbances, unfavourable changes in haemostatic parameters and lack of bone mass.

The term "androgenic component" is defined as a substance that is capable of triggering an androgenic response in vivo or a precursor which is capable of liberating such a substance in vivo. Usually androgenic components are capable of binding to an androgen receptor.

Androgenic components that may suitably be employed in the present method may be selected from the group consisting of dehydroepiandrosterone (DHEA), danazol, gestrinone, testosterone esters, precursors capable of liberating these androgens when used in the present method and mixtures thereof. Preferably the testosterone esters employed comprise an acyl group which comprises at least 6, more preferably from 8-20 and preferably 9-13 carbon atoms. The androgens that can be used most advantageously in the present method are DHEA and/or testosterone undecanoate.

It is noted that, for instance, DHEA and testosterone undecanoate are precursors of testosterone and that said precursors per se exhibit virtually no affinity for androgen receptors in the female body. The effectiveness of the androgens within the method of the invention is determined by their functionally active form, which may well be different from the form in which they are administered.

In a preferred embodiment the androgen is provided in an amount equivalent to a daily oral dosage of 5 to 250 mg DHEA, which is equivalent to a daily oral dosage of 1 to 50 mg testosterone undecanoate. More preferably the androgen is provided in an amount which is equivalent to a daily oral dosage of 10-120 mg DHEA. Most preferably the androgen is administered in an amount which is equivalent to a daily oral dosage of 20-60 mg DHEA.

In order to obtain the desired impact from the present method it is advisable to administer the dosage units in an amount which leads to an increase in blood serum androgen level of no more than 5 nmole testosterone equivalent per liter, preferably less than 3 nmole testosterone equivalent per liter and most preferably less than 1.5 nmole testosterone equivalent per liter.

The present method preferably does not employ a gonadotropin hormone releasing hormone composition as described in the aforementioned patents U.S. Pat. No. 5,211,952, U.S. Pat. No. 5,340,584 and U.S. Pat. No. 5,340,585. Similarly, the present method preferably does not employ a luteinizing hormone releasing hormone composition as described in U.S. Pat. No. 4,762,717 and U.S. Pat. No. 5,130,137. Furthermore, the present method preferably does not comprise the co-administration of an anti-progestogen as described in U.S. Pat. No. 5,468,736. The method may also suitably be applied without the co-administration of an anti-sense oligonucleotide that is complementary to the nucleotide sequence of the follicle stimulating hormone (FSH) receptor (WO 00/73416).

The present method is not suitable for oophorectomised females or for females in whom endometrial stimulation by estrogenic compositions is minimised or absent, e.g. as a result of hysterectomy.

Another aspect of the invention relates to a contraceptive kit comprising at least 20 oral dosage units that contain the estrogenic component as defined herein before and/or the progestogenic component as described herein before, wherein at least 10 units contain between 0.01 and 20 mg, preferably between 0.05 and 10 mg of the estrogenic component and at least 10 units contain the progestogenic component in an amount equivalent to 30-750 μg levonorgestrel. In the present kit, the progestogenic component may conveniently be combined with the estrogenic component in a single dosage unit. Accordingly, the kit preferably comprises at least 10 dosage units which contain between 0.01 and 20 mg of the estrogenic component and the progestogenic component in an amount equivalent to 30-750 μg levonorgestrel.

A pharmaceutical kit that is particularly suitable for use in combined and sequential methods will usually comprise 20-35 oral dosage units, wherein 10-35 units contain a combination of the estrogenic component and the progestogenic component in the indicated amounts, 0-25 units contain no progestogenic component and the estrogenic component in the indicated amounts, and 0-8 units contain no estrogenic component and no progestogenic component.

A pharmaceutical kit that is particularly suitable for use in a continuous combined regimen or a combined regimen comprises at least 20 oral dosage units which either contain the combination of the progestogenic and the estrogenic component or neither of these two components (placebo's) and of which dosage units at least 15, preferably at least 20 contain the combination of the estrogenic component and the progestogenic component and 0-8 contain no estrogenic component and no progestogenic component. If such a kit is to be used in a continuous combined method, the kit may advantageously comprise at least 28, preferably at least 60 dosage units, all of which dosage units contain the combination of the estrogenic component and the progestogenic component in the amounts indicated above.

In case the present kit is meant to be used in a contraceptive protocol that employs an administration free interval so as to induce menses (e.g. a combined method or a sequential method with pause) the kit will usually comprise at least 3 units, preferably at least 5 units that contain no estrogenic component and no progestogenic component.

In a particularly preferred embodiment of the invention the present kit is designed for use in a sequential method. Such a kit will usually comprise 20-35 oral dosage units wherein 10-32 units contain the combination of the estrogenic component and the progestogenic component, and 3-18 units contain the estrogenic component and no progestogenic component. Particularly preferred is a kit that is designed for use in a sequential method without a significant pause. In such a kit, which will usually comprise 20-35 oral dosage units, 10-20 units contain a combination of the estrogenic component and the progestogenic component, 10-18 units contain the estrogenic component and no progestogenic component and at most 1 unit contains no estrogenic component and no progestogenic component.

The pharmaceutical kits according to the present invention will normally contain only one or more of the following types of oral dosage units: units that contain the combination of the estrogenic and the progestogenic component; units that contain the estrogenic component and no progestogenic component; and units that effectively function as placebo's. Preferably the kit comprises at least 20 units that contain the combination of the estrogenic and the progestogenic component or the estrogenic component and no progestogenic component.

If the present kit is to be used in a combined or sequential protocol, the oral dosage units are preferably arranged within the kit in a fixed sequence corresponding to the intended order of administration. Data indications may be provided on the packaging. The packaging may be a tube or box or a strip. The box may be circular, square, or otherwise shaped with the tablets being accommodated separately therein for ease of administration. Date indications may appear adjacent to each tablet corresponding with the days on which each tablet is to be taken. Some indication of the sequence in which the tablets are to be taken preferably appears on the packaging regardless of its form.

Generally speaking, the oral dosage units in the present kit are prepared according to well known pharmaceutical procedures. The active ingredient(s) are combined with a pharmaceutically acceptable excipient and converted into a pharmaceutically acceptable form for oral administration, e.g. a tablet, capsule, cachet, pellet, pill, powder or granules. The excipient may include appropriate pharmaceutical carriers such as diluents, binders and lubricants. For example gums, starches and sugars are commonly used as pharmaceutical carriers. Tablets and other oral dosage units can suitably contain materials such binders (e.g. hydroxypropylmethyl cellulose, polyvinyl pyrrolidine, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc).

The active ingredient(s) may comprise from about 0.01% by weight to about 50% by weight of the formulation in the dosage unit, the remainder consisting of excipient. The active ingredient(s) are compounded with the chosen carrier and in for example the case of a tablet form, placed in a tablet moulding apparatus to form the tablets. Alternatively the compounded material may be incorporated as a powder or granules in a capsule. Various other options that may suitably be used in accordance with the present invention are well known to the person skilled in the pharmaceutical art.

The present invention is further illustrated by the following examples, which, however, are not to be construed as limiting. The features disclosed in the foregoing description, in the following examples and in the claims may, both separately and in any combination thereof, be material for realising the invention in diverse forms thereof.

EXAMPLES

Example 1

Vaginal cornification was chosen as a tissue-specific and estrogen-sensitive endpoint to determine the estrogenicity of estetrol (E4), after oral administration, in hypoestrogenic rats. 17α-ethinylestradiol (EE) and vehicle (10% ethanol/sesame oil) served as controls in the bioassay.

Uterine weight increase in the rat is more commonly used as a measure of estrogenicity. However, uterine weight also responds to progesterone, testosterone, and other agents not characteristically regarded as estrogens. In the early 1920s it was discovered that follicular fluid from the pig ovary contained a factor(s) that caused cornification/keratinization of the vaginal epithelium in the rat (Allen and Doisy, 1923, JAMA, 81, 819-821; Allen and Doisy, 1924, Am. J. Physiol., 69, 577-588). The so-called vaginal cornification response in rats subsequently provided a bioassay for testing estrogenicity. Vaginal epithelial cornification/keratinization in ovariectomized rats can be produced only by compounds considered to be true estrogens (Jones et al, 1973, Fert. Steril. 24, 284-291). Vaginal epithelial cornification/keratinization represents, therefore, a highly selective endpoint to determine the potency of estrogens (Reel et al., 1996, Fund. Appli. Toxicol. 34, 288-305).

Adult intact female CD rats were ovariectomized to induce estrogen deficiency. Vaginal lavages were performed daily for seven days to ensure that the rats demonstrated castrate vaginal smears (predominance of leukocytes in the vaginal smear, and similar in to appearance to a diestrous vaginal smear). Castrate vaginal smears are indicative that complete ovariectomy was achieved. Treatment commenced following completion of the 7 days of smearing (day 0=first day of dosing). Animals were dosed, once daily for 7 consecutive days. Daily vaginal lavages continued to be obtained for 7 days after dosing was initiated in order to detect vaginal cornification, as an indication of an estrogenic response. A drop of vaginal washings was placed on a glass slide and examined by light microscopy to detect the presence or absence of cornified epithelial cells. Vaginal lavages were obtained prior to dosing on days 0-6 and prior to necropsy on day 7.

The vaginal cornification bioassay was performed in order to determine the estrogenic profile of E4 when given orally (po) to ovariectomized adult rats. EE was used as a positive control. The vehicle (10% ethanol/sesame oil) served as the negative control. Steroids were dissolved in absolute ethanol and then brought to the final concentration with sesame oil (10% ethanol in sesame oil). A vaginal estrogenic response occurred in all rats (8/8) given 50 µg/kg/day EE po by day 7 (FIG. 2). Similarly, vaginal epithelial cornification was observed in all rats (8/8) treated po with either 0.1, 0.3, 1.0, or 3.0 mg/kg/day E4 by day 7 (FIG. 2), whereas animals treated with the vehicle did not exhibit vaginal epithelial cornification (0/8). Even in rats given relatively low doses of E4 (e.g. 0.1 and 0.3 mg/kg/day), the onset of vaginal cornification (defined as the amount of animals responding at days 1-3 of the study) was as fast as in EE-treated animals (FIG. 2), demonstrating estetrol's superb bioavailability characteristics after oral administration.

Example 2

A bioassay method (modified according to De Visser et al., 1984, Arzneim. Forsch. 34, 1010-1020) was chosen to determine the antiovulatory activity of estetrol (E4), after oral administration, in four-day cyclic rats. 17α-ethinylestradiol (EE), 17β-estradiol (E2) and vehicle (10% ethanol/sesame oil) served as controls in the bioassay.

Rats are spontaneously ovulating, polyestrous mammals. Generally, proestrus lasts for 12 to 14 hours, estrus for 25 to 27 hours, metestrus for 6 to 8 hours, and diestrus for 55 to 57 hours (Freeman, 1988, In: The Physiology of Reproduction, E Knobil and J Neill (eds). Raven Press, Ltd, New York, pp. 1893-1928). These stages of the estrous cycle can be classified based on the cell types present in daily vaginal smears (Schwartz, 1969, Recent Prog. Horm. Res. 25, 1-55).

The preovulatory period of the rat estrous cycle is characterized by ovarian follicular growth and enhanced estrogen secretion. In the four-day cyclic rat, peripheral plasma levels of E2 are basal through estrus. At the end of metestrus and extending through early diestrus, plasma levels of E2 begin to rise. This increase continues through diestrus and early proestrus to reach peak values and plateau by mid-proestrus. Subsequently, E2 levels fall rapidly, reaching basal values by the early morning hours of estrus. The rising estrogen levels from late metestrus to early proestrus exert a positive feedback effect on the hypothalamic-pituitary axis resulting in a luteinizing hormone (LH) surge on the afternoon of proestrus. The LH surge induces follicular rupture and the release of ova in the early morning hours of estrus. By early afternoon on the day of estrus, ova are present in the ampulla of the oviduct and are readily visualized under a dissecting microscope.

Progesterone or levonorgestrel administered subcutaneously on diestrus to four-day cyclic rats is known to inhibit ovulation and increased the estrous cycle length in a dose-dependent manner (Beattie and Corbin, 1975, Endocrinology 97, 885-890). It was shown that the progestational block of ovulation takes place predominately via the hypothalamic-pituitary axis. Retardation of follicular growth accompanies ovulatory inhibition at high doses of progestogen when both serum follicle stimulating hormone (FSH) and LH are significantly reduced (Beattie and Corbin, 1975, Endocrinology 97, 885-890). De Visser et al. (1984, (Arzneim. Forsch. 34, 1010-1020) have found that oral administration of EE to rats beginning on the day of estrus and continuing through the estrous cycle blocked ovulation in a dose-dependent manner.

Vaginal smears from female rats were obtained daily for two weeks to identify four-day cycling rats. Only four-day cyclic rats were used for the antiovulatory bioassay. At approximately 6:30 am and 4:30 pm on the day of estrus, rats were dosed orally with EE, E2, E4 or vehicle control (10% ethanol/sesame oil). Twice daily dosing continued for an additional 3 consecutive days. One day after the final dose (day 5), the rats were euthanized by $CO_2$ asphyxiation at approximately 1 pm, and the number of ova per oviduct was determined and recorded. Group means were calculated for the number of ova per ovulated rat (both oviducts). The ratio of rats ovulating for each treatment group was compared to the ratio for the vehicle-treated rats. Dose-dependent effects on the ratio of rats ovulated to rats treated were used to calculate an $ED_{50}$ for EE, E2 and E4.

Eight of 8 rats ovulated when treated po with vehicle control twice daily over the 4 days of the estrous cycle, whereas rats that received EE, E2 or E4, po, displayed dose-dependent antiovulatory activity. Twice daily po doses of 0.3 and 1 µg EE/kg for 4 days were ineffective in inhibiting ovulation, whereas twice daily po doses of 3 µg EE/kg blocked ovulation in 1 of 8, 10 µg EE/kg in 4 of 8, and 30 µg EE/kg in 8 of 8 rats. Hence, the antiovulatory $ED_{50}$ for EE administered po twice daily for 4 days was calculated as 10 µg/kg.

Twice daily po doses of 30 µg E2/kg for 4 days were ineffective in inhibiting ovulation, whereas twice daily po doses of 100 µg E2/kg blocked ovulation in 7 of 8, and 300, 1000, or 3000 µg E2/kg twice daily blocked ovulation in 8 of 8 rats. The steepness of the dose-response for E2 prevented exact calculation of the $ED_{50}$ value. However, it was clear that the antiovulatory $ED_{50}$ for E2 administered po twice daily for 4 days was in the range of 30 to 100 µg/kg.

Twice daily po doses of 30 µg E4/kg for 4 days failed to inhibit ovulation, whereas 100 µg E4/kg blocked ovulation in 2 of 8, 300 µg E4/kg in 5 of 8, 1000 µg E4/kg in 7 of 8, and 3000 µg E4/kg in 8 of 8 rats. Hence, the antiovulatory $ED_{50}$ for E4 administered po twice daily for 4 days was calculated as 182 µg/kg. Based on these data it is clear that E4 approximates the antiovulatory potency of E2 and is "only" 18 times less potent than the synthetic estrogen, ethinylestradiol, under the study conditions tested.

Example 3

To evaluate the oral bioavailability of estetrol (E4) and to determine the elimination half-life, single oral (po) and subcutaneous (sc) dose studies were performed in female Sprague Dawley rats followed by frequent blood sampling over a 24 hours interval.

Female Sprague Dawley rats were equipped with a permanent silatic heart catheter, as described by Kuipers et al. (1985, Gastroenterology, 88, 403-411). Rats were allowed to recover from surgery for 5 days and were than administered 0.05, 0.5, or 5 mg/kg E4 in 0.5 ml arachidis oil. For sc administration, E4 was injected in the neck area using a 1 ml syringe and 20 g needle. For po administration of E4, rats were lightly anaesthesized with halothene/$N_2O/O_2$ and E4 was directly applied intragastrically using a plastic stomach intubator. Blood samples were subsequently collected via the heart catheter in heparinized tubes at 0.5, 1, 2, 4, 8 and 24 hours. Erythrocytes were removed by centrifugation at 5000×g for 10 minutes at 4° C. and blood plasma was stored at −20° C. After thawing the plasma samples, liquid-liquid extraction (hexane and diethyl ether) was employed to prepare the E4-containing plasma samples for HPLC analysis (Perkin Elmer 200) and tandem mass spectrometry using a PE Sciex 3000 tandem mass spectrometer and APCI interface. With each sample batch, a calibration curve with 6 calibrators was recorded. The calibration curve was calculated using linear regression (correlation coefficient >0.98), which permitted quantitation of plasma concentrations. For each rat plasma, sampled at different time intervals, data were collected.

Plasma E4 concentration data were analysed with "WinNonLin, edition 3.1" and involved pharmacokinetic parameters for $C_{max}$, half-life and $AUC_{0-24}$. Especially, using the lower and intermediate dose levels of 0.05, 0.5 mg/kg, E4 demonstrated an oral bioavailability equal to the bioavailability obtained with sc administration (80-100%). At the highest dose level tested, 5.0 mg/kg E4, absorption kinetics gave rise to an oral bioavailability approximating 30-60% of sc administered E4. Interestingly, E4 demonstrated a relatively long half-life of 2-3 hours, enabling the detection of bioactive levels of unconjugated E4 at all time points over a 24 hour interval.

Example 4

An established competitive steroid-binding assay (Hammond and Lahteenmaki. 1983. Clin Chem Acta 132:101-110) was used to determine the relative binding affinity of estetrol (E4), 17α-ethinylestradiol(EE2), 17β-estradiol (E2), testosterone (T) and 5α-dihydrotestosterone (DHT) for human sex Hormone Binding Globulin (SHBG).

Human SHBG was purified from transgenic mouse serum, as described previously (Avvakumov G V et al., 2000. J Biol Chem 275: 25920-25925). The human SHBG prepared in this way was assessed to be >99% pure by polyacrylamide gel electrophoresis under denaturing conditions. Its steroid-binding characteristics are indistinguishable from SHBG in human serum (Avvakumov G V et al., 2000. J Biol Chem 275: 25920-25925). The in vitro assay involved the use of the purified human SHBG and [³H]DHT or [³H]estradiol as labeled ligands. Human SHBG was treated for 30 min at room temperature with a dextran-coated charcoal (DCC) suspension in phosphate buffered saline (PBS) to remove any steroid ligand. After centrifugation (2,000×g for 10 min) to sediment the DCC, the supernatant containing the human SHBG was diluted in PBS to a concentration of 1 nM based on its steroid binding capacity.

Figure 3:
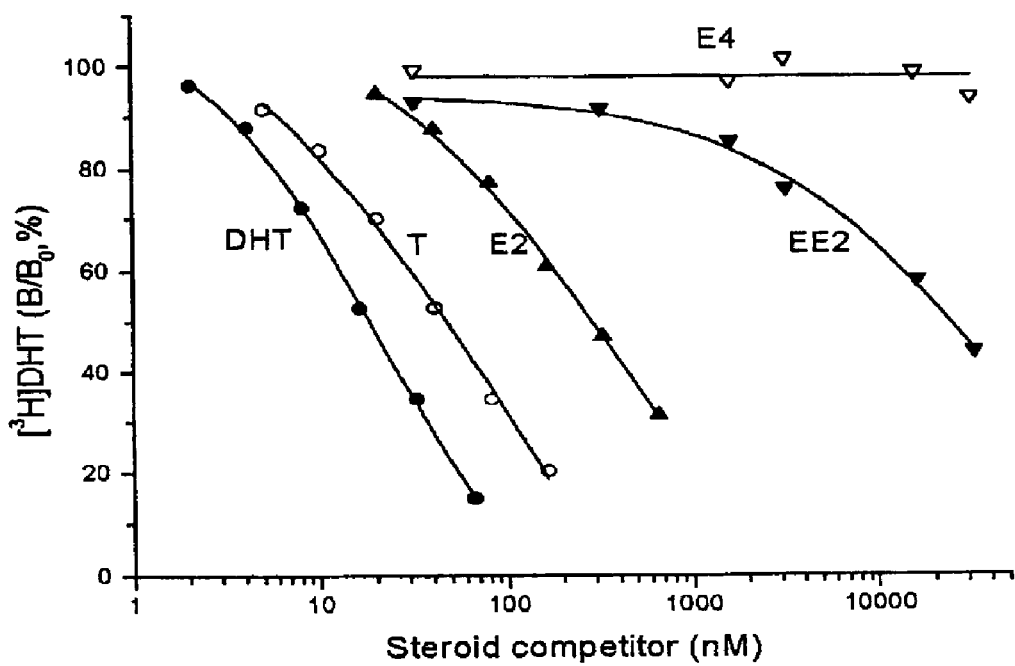
FIG. 3 is a chart showing competitive displacement of [$^3$H]DHT (panel A) and [$^3$H]estradiol (panel B) from the human sex hormone-binding globulin steroid binding site. The unlabeled steroid ligands used as competitors were as follows: estetrol (E4), 17α-ethinylestradiol (EE2), 17β-estradiol (E2), testosterone (T) and 5α-dihydrotestosterone (DHT).
Figure 3:
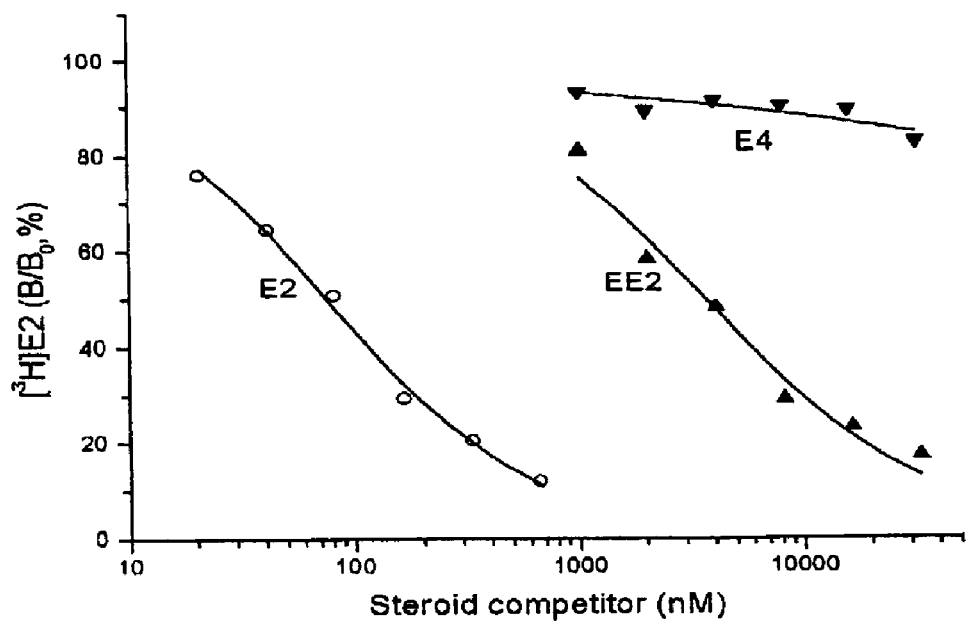

Duplicate aliquots (100 µl) of this human SHBG solution were then incubated with an equal volume of either [³H]DHT or [³H]estradiol at 10 nM, together with 100 µl of PBS alone or the same amount of PBS containing increasing concentrations of unlabeled steroid ligands as competitors in polystyrene test tubes. After incubation for 1 h at room temperature the reaction mixtures were placed in an ice bath for a further 15 min. Aliquots (600 µl) of an ice cold suspension of DCC were then added to each tube, and after a brief 2 seconds mixing, each tube was incubated in an ice bath for either 10 min or 5 min depending on whether [³H]DHT or [³H]estradiol were being used as labeled ligands, respectively. The unbound ligands adsorbed to DCC were then removed by centrifugation (2,000×g for 15 min at 4 C), and the amounts of [³H]labeled ligands bound to SHBG were counted in 2 ml ACS scintillation cocktail using in liquid scintillation spectrophotometer. The average amounts of [³H]labeled ligands bound to SHBG at each concentration of competitor (B) were expressed as a percentage of the average amounts of [³H] labeled ligands bound to SHBG in the absence of competitor ($B_0$), and were plotted against the concentration of competitor in each assay tube. The results of the competitive binding assays are depicted in FIG. 3.

As is clearly apparent from these competitive binding assays, estetrol does not bind at all to human SHBG when tested with either [³H]DHT or [³H]estradiol as labeled ligands. This is in marked contrast with reference steroids ethinylestradiol, 17β-estradiol, testosterone and 5α-dihydrotestosterone, which, in this order, show an increased relative binding affinity for human SHBG. Importantly, estetrol binding to SHBG was negligible when compared with the other estrogens tested, ethinylestradiol and 17β-estradiol.

Example 5

The present estrogenic components may suitably be processed, together with additives, excipients and/or flavouring agents customary in galenic pharmacy, in accordance with the conventional methods into the usual forms of administration. For oral administration, suitable are, in particular, tablets, dragees, capsules, pills, suspensions, or solutions.

| | |
|---|---|
| Estetrol | 1.500 g |
| Levonorgestrel | 0.150 g |
| Polyvinylpyrrolidone (Kollidon 25 ® ex BASF) | 13.500 g |
| Lactose | 135.645 g |
| Microcrystalline cellulose (Avicel PH 101 ®) | 26.250 g |
| Glyceryl palmitostearate (Precirol ®) | 2.775 g |
| Anhydrous colloidal silica (Aerosil 200 ®) | 1.000 g |
| Crospovidone (Polyplasdone XL ®) | 4.000 g |
| Coloring agent | 0.180 g |

Tablets that additionally contain 50 mg dehydroepiandrosterone may be prepared from a similar formulation.

The invention claimed is:
1. A contraceptive method, comprising administering orally an estrogenic component and a progestogenic component to a mammalian female of childbearing capability in an effective amount to inhibit ovulation, said estrogenic component being selected from the group consisting of substances represented by the following formula:

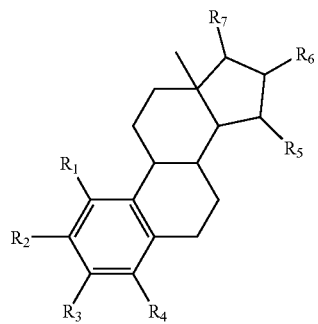

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;
  precursors capable of liberating a substance according to the aforementioned formula when used in the present method, which precursors are derivatives of the aforementioned estrogenic substances wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and mixtures of one or more of the aforementioned substances or precursors,
wherein the method does not employ co-administration of an LHRH composition.

2. The method according to claim 1, wherein the progestogenic component is administered in an amount which is equivalent to a daily oral dosage of 0.3 to 20 µg levonorgestrel per kg of bodyweight.

3. A pharmaceutical kit comprising at least 20 oral dosage units, wherein at least 10 units contain between 0.01 and 20 mg of an estrogenic component and at least 10 units contain a progestogenic component in an amount equivalent to 30-750 µg levonorgestrel, said estrogenic component being selected from the group consisting of substances represented by the following formula:

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;
   precursors capable of liberating a substance according to the aforementioned formula when used in the present method, which precursors are derivatives of the aforementioned estrogenic substances wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and
   mixtures of one or more of the aforementioned substances or precursors, wherein the oral dosage units do not contain an LHRH composition.

4. The pharmaceutical kit according to claim 3, comprising at least 10 oral dosage units that contain between 0.01 and 20 mg of the estrogenic component and contain the progestogenic component in an amount equivalent to 30-750 µg levonorgestrel.

5. The pharmaceutical kit according to claim 4, comprising at least 20 oral dosage units containing the combination of the estrogenic component and the progestogenic component.

6. The pharmaceutical kit according to claim 4, comprising from 20-35 oral dosage units, wherein 10-35 units contain the combination of the estrogenic component and the progestogenic component in the indicated amounts, 0-25 units contain no progestogenic component and the estrogenic component in the indicated amounts, and 0-8 units contain no estrogenic component and no progestogenic component.

7. The pharmaceutical kit according to claim 4, wherein the kit comprises at least 28 oral dosage units and all the included dosage units contain the combination of the estrogenic component and the progestogenic component.

8. The pharmaceutical kit according to claim 3, wherein the kit comprises at least 3 oral dosage units that contain no estrogenic component and no progestogenic component.

9. The pharmaceutical kit according to claim 4, wherein 10-32 oral dosage units contain the combination of the estrogenic component and the progestogenic component, and 3-18 units contain the estrogenic component and no progestogenic component.

10. The pharmaceutical kit according to claim 9, wherein 10-20 oral dosage units contain the combination of the estrogenic component and the progestogenic component, 10-18 units contain the estrogenic component and no progestogenic component, and at most 1 unit contains no estrogenic component and no progestogenic component.

11. The method according to claim 1, wherein the administration of the estrogenic component and the progestogenic component is in an amount effective to inhibit ovulation during a period of at least 20 days.

12. The method according to claim 1, wherein $R_3$ represents a hydroxyl group or an alkoxy group.

13. The method according to claim 1, wherein 3 of the groups $R_1$, $R_2$, $R_3$ and $R_4$ represent hydrogen atoms.

14. The method according to claim 1, wherein the method comprises uninterrupted oral administration of the estrogenic component during a period of at least 10 days.

15. The method according to claim 1, wherein the method comprises uninterrupted oral administration, during a period of at least 10 days, of a combination of the estrogenic component and the progestogenic component.

16. The method according to claim 1, wherein the method comprises uninterrupted oral administration of a combination of the estrogenic component and the progestogenic component during a period of at least 20 days.

17. The method according to claim 1 further comprising, wherein the method comprises uninterrupted oral administration of a combination of the estrogenic component and the progestogenic component during a period of at least 28 days.

18. The method according to claim 15 wherein the method comprises an interval of at least 2 days, during which no progestogenic component and no estrogenic component is administered and wherein the resulting decrease in serum concentration of the progestogenic component and the estrogenic component induces menses.

19. The method according to claim 15, wherein the method comprises uninterrupted oral administration of the estrogenic component during a period of at least 28 days and wherein, following the combined administration of the estrogeriic component and the progestogenic component, the estrogenic component and no progestogenic component are administered during 3-18 consecutive days and the resulting decrease in serum concentration of the progestogenic component induces menses.

20. The method according to claim 1, wherein the method comprises at least once daily oral administration of the estrogenic component and the progestogenic component during a period of at least 10 days.

21. The method according to claim 1, wherein the estrogenic component is orally administered in an amount of less than 1 mg per kg of bodyweight per day.

22. The method according to claim 1, wherein the estrogenic component is orally administered in an amount of at least 1 µg per kg of bodyweight per day.

* * * * *